United States Patent [19]

Ahn

[11] Patent Number: 4,981,852

[45] Date of Patent: Jan. 1, 1991

[54] CHEMICAL COMPOUNDS TRIAMTERENE AND HYDROCHLOROTHIAZIDE

[75] Inventor: Kap S. Ahn, Northbrook, Ill.

[73] Assignee: Multilan AG, Switzerland

[21] Appl. No.: 193,890

[22] Filed: May 13, 1988

[51] Int. Cl.$^5$ .................. A61K 9/08; A61K 31/50; A61K 31/41; A01N 43/58

[52] U.S. Cl. ................... 514/249; 514/255; 514/256; 514/363; 514/869; 514/941

[58] Field of Search .................. 424/451, 456, 485; 514/249, 155, 258, 363, 369, 388, 869, 941, 255, 256

[56] References Cited

U.S. PATENT DOCUMENTS

| | | | |
|---|---|---|---|
| 3,081,230 | 3/1963 | Weinstock et al. | 514/223.5 |
| 3,901,971 | 8/1975 | Cohen et al. | 424/487 |
| 4,255,413 | 3/1981 | Rattie | 424/452 |
| 4,285,947 | 8/1981 | Higuchi et al. | 514/155 |
| 4,425,344 | 1/1984 | Horlington | 514/249 |
| 4,425,345 | 1/1984 | Horlington | 514/249 |
| 4,526,777 | 7/1985 | Blume et al. | 424/458 |
| 4,547,498 | 10/1985 | Blume et al. | 514/223.5 |
| 4,795,643 | 1/1989 | Seth | 424/456 |

OTHER PUBLICATIONS

Physician's Desk Reference, pp. 1801–1803 (1987).

*Primary Examiner*—Merrell C. Cashion, Jr.
*Assistant Examiner*—Carlos Azpuru
*Attorney, Agent, or Firm*—Emrich & Dithmar

[57] ABSTRACT

A diuretic pharmaceutically acceptable solution of triamterene and solutions of triamterene and hydrochlorothiazide to provide an antihypertensive and diuretic effect for those in need thereof. Triamterene is solubilized in a combination of a glycol and lactic acid present in an amount sufficient to maintain the triamterene in solution. A pharmaceutically acceptable diluent, such as glycerin is also present.

22 Claims, No Drawings

CHEMICAL COMPOUNDS TRIAMTERENE AND HYDROCHLOROTHIAZIDE

BACKGROUND OF THE INVENTION invention relates to novel medicinal compositions having substantial diuretic and/or antihypertensive activities. The invention relates to two solutions, one of triamterene and the other, a solution of triamterene and hydrochlorothiazide.

Triamterene is 2,4,7-triamino-6-phenylpteridine. Hydrochlorothiazide is 6-chloro-3,4-dihydro-2H-1,2,4-benzothiadiazine-7-sulfonamide 1,1-dioxide. Triamterene is a diuretic and the combination of triamterene and hydrochlorothiazide is a diuretic with antihypertensive properties. As is known, the hydrochlorothiazide component blocks the reabsorption of sodium and chloride ions thereby increasing the quantity of sodium traversing the distal tubule and the volume of water excreted. Although the exact antihypertensive effect of hydrochlorothiazide is not known, the continued use of the drug decreases the excretion of uric acid and may increase the excretion of iodide and may also reduce glomerular filtration rate. The triamterene exerts its diuretic effect as does hydrochlorothiazide except that it only inhibits the reabsorption of sodium in exchange for potassium and hydrogen ions.

Both of the drugs exhibit approximately the same duration of effectiveness in that they both have peak activity at two to three hours after ingestion with tapering effectiveness during the subsequent seven to nine hours. The combination of both triamterene and hydrochlorothiazide finds particular usefulness in the treatment of edema and has been indicated as injunctive therapy associated with congestive heart failure, hepatic cirrhosis and the nephrotic syndrome. General dosage has been set at 100 mg triamterene and 100–200 mg triamterene and 50–100 mg hydrochlorothiazide in divided doses. The drug is available in solid form administered as capsules.

It has now been discovered that a liquid form of triamterene and/or a liquid form of triamterene and hydrochlorothiazide may be delivered. It is important to provide an oral solution because it is easier to administer and for some easier to ingest. Heretofore, a solution has not been available because triamterene is extremely insoluble and has not been able to be put into a stable solution capable of being ingested as a pharmaceutical preparation.

Accordingly, it is an object of the present invention to provide a pharmaceutically acceptable solution of triamterene.

It is another object of the present invention to provide a pharmaceutically acceptable solution of triamterene and hydrochlorothiazide capable of being administered orally.

The invention contemplates the solubilization of triamterene in a combination of glycols and lactic acid. It has been found that either the presence of lactic acid or an acid salt thereof alone is insufficient to cause triamterene to be solubilized, and it has been found that the combination of triamterene and glycol or combinations of propylene glycol and polyethylene glycol is insufficient to cause the triamterene to go into solution. However, it has been found that a combination of glycol and lactic acid or an acid salt thereof when combined with triamterene causes the triamterene to become soluble. This solubilization of triamterene remains effective even when mixed with hydrochlorothiazide.

In a commercial solution, various preservatives such as methylparaben and sodium benzoate or propylparaben or benzoic acid or other known preservatives which are pharmaceutically acceptable or various combinations thereof may be used as required and is well known. In addition, a wide variety of colors and flavors as well as various combinations of flavors and colors may also be used in a commercial preparation. For instance, sodium saccharin may be used as a sweetening agent and various colors all of which must be pharmaceutically acceptable may be used in the product. The presence of various preservatives, sweetening agents, flavors and colors do not form any part of the invention but may be included in a commercial preparation.

A diluent or carrier is provided in the commercial embodiment. The diluent or carrier which is preferred is glycerin, but other well known diluents that are pharmaceutically acceptable carriers may be substituted for glycerin without affecting the efficacy of the invention. Generally, glycerin or other pharmaceutically acceptable carrier or diluent should be present in the range of from about 0.5% by volume to about 55% by volume. The preferred concentration of diluent or carrier is in the range of from about 20% by volume to about 50% by volume. It is also contemplated that buffers may be required; however, at present it appears that buffers are not required. The optimum pH range for the solution is from about 4.0 to 6.0. If buffers are required for a commercial solution, it is within the scope of the invention.

As a required element of the invention, glycols must be present. While a large variety of glycols may be useful, propylene glycol and/or polyethylene glycol are preferred. Generally, glycols having a molecular weight from about 200 to about 6000 are preferred and are selected from various combinations of propylene glycol or polyethylene glycol. Glycol should be present in the solution in a concentration in the range of from about 1% by volume to about 50% by volume. While propylene glycol may be used alone, it may be used in combination with as much as 50% polyethylene glycol. A requirement for the solubilization of triamterene is the presence of both glycol and lactic acid or a acid salt thereof. It has been found that with the amount of glycol required as stated above, lactic acid should be present in the amount of 2% for each 1% triamterene, and it has been found that the amount of lactic acid must be proportionally increased if the concentration of triamterene is increased or the amount of lactic acid may be proportionally decreased if the concentration of triamterene is decreased. For instance, if triamterene having a concentration of 5 mg/ml is used, then the amount of lactic acid required is 1%. Generally, lactic acid may be present in the range of from about 0.5% to about 20%.

Various commercial formulas have been prepared and the procedure has been as follows. An amount of polyethylene glycol-600 and propylene glycol has been added to a main tank and agitated. Thereafter the triamterene is added to the glycol and agitated but none of the triamterene is dissolved. Thereafter the lactic acid in the above specified amount is added with continued agitation which causes the triamterene to dissolve.

In a separate container the hydrochlorothiazide and methylparaben is dissolved in propylene glycol and a polyethylene glycol combination which is warmed to about 50° C. Then the combination of glycol, hydrochlorothiazide and methylparaben is added to the main tank containing the dissolved triamterene. Thereafter in a separate container the sodium benzoate is warmed in purified water to a temperature of between 40° and 45° C. and added to the main tank which is continually agitated.

Thereafter, the sodium saccharin is added to a warmed (45°—45° C.) quantity of glycerin and then both are added to the main tank which has been continually agitated. Finally, the remainder of the glycerin is added. Various flavors may be added such as chocolate extract or other additives such as raspberry oil and anise oil dissolved in or mixed with propylene glycol. At this point the coloring solution may be added such as FD&C Red #40 in purified water and may be filtered and added to the main tank which is under continual agitation. Then, the total batch volume may be diluted with glycerin, and mixed for no less than about thirty minutes, if the batch volume is 900 gallons or less. If the batch volume is over 900 gallons, mixing should be continuous for about sixty minutes.

As before stated, several examples of dissolved triamterene and combinations of triamterene and hydrochlorothiazide in solution capable for oral administration have been prepared and examples are hereinafter set forth.

Product: TRIAMTERENE ORAL SOLUTION
Potency: Triamterene

| Ingredient(s) | 50 mg/5 ml | | 25 mg/5 ml | |
|---|---|---|---|---|
| | Ex. #1 | Ex. #3 | Ex. #2 | Ex. #4 |
| Propylene Glycol (A) | 10% | 50% | 10% | 50% |
| Polyethylene Glycol-600 | 40% | — | 40% | — |
| Triamterene | 1% | 1% | 0.5% | 0.5% |
| Lactic Acid (85%) | 2% | 2% | 1% | 1% |
| Hydrochlorothiazide | — | — | — | — |
| Methylparaben | 0.1% | 0.1% | 0.1% | 0.1% |
| Propylene Glycol (B) | 1% | 1% | 1% | 1% |
| Polyethylene Glycol-400 | — | — | — | — |
| Polyethylene Glycol-600 | 4% | 4% | 4% | 4% |
| Sodium Benzoate | 0.1% | 0.1% | 0.1% | 0.1% |
| Purified Water (A) | 0.5% | 0.5% | 0.5% | 0.5% |
| Glycerin | 30% | 30% | 30% | 30% |
| Sodium Saccharin | 0.5% | 0.5% | 0.5% | 0.5% |
| Purified Water (B) | — | — | — | — |
| Chocolate Extract | 0.12% | 0.12% | 0.12% | 0.12% |
| Raspberry Oil | 0.02% | 0.02% | 0.02% | 0.02% |
| Anise Oil | 0.01% | 0.01% | 0.01% | 0.01% |
| Propylene Glycol (C) | 2% | 2% | 2% | 2% |
| FD&C Yellow #6 | 0.002% | 0.002% | — | — |
| FD&C Red #40 | — | — | 0.006% | 0.006% |
| Purified Water (C) | 0.2% | 0.2% | 0.6% | 0.6% |
| Citric Acid | — | — | 0.32% | 0.32% |
| Sodium Citrate | — | — | — | — |
| Glycerin | to 100% | to 100% | to 100% | to 100% |
| pH Found | 4.94 | 4.95 | 5.00 | 5.00 |

Product: TRIAMTERENE AND HYDROCHLOROTHIAZIDE ORAL SOLUTION
Potency: Triamterene 50 mg/5 ml, Hydrochlorothiazide 25 mg/5 ml

| Ingredient(s) | Ex. #5 | Ex. #6 | Ex. 7 |
|---|---|---|---|
| Propylene Glycol (A) | 50% | 10% | 50% |
| Polyethylene Glycol-600 | — | 40% | — |
| Triamterene | 1% | 1% | 1% |
| Lactic Acid (85%) | 2% | 2% | 2% |
| Hydrochlorothiazide | 0.5% | 0.5% | 0.5% |
| Methylparaben | 0.1% | 0.1% | 0.1% |
| Propylene Glycol (B) | — | 1% | — |
| Polyethylene Glycol-400 | 10% | — | 10% |
| Polyethylene Glycol-600 | — | 4% | — |
| Sodium Benzoate | 0.1% | 0.1% | 0.1% |
| Purified Water (A) | 0.38% | 0.5% | 0.5% |
| Glycerin | 30% | 30% | 30% |
| Sodium Saccharin | 0.5% | 0.5% | 0.5% |
| Purified Water (B) | 0.5% | 0.5% | 0.5% |
| Chocolate Extract | — | 0.12% | 0.12% |
| Raspberry Oil | — | 0.02% | 0.02% |
| Anise Oil | — | 0.01% | 0.01% |
| Propylene Glycol (C) | — | 2% | — |
| FD&C Yellow #6 | — | 0.002% | 0.002% |
| FD&C Red #40 | — | — | — |
| Purified Water (C) | — | 0.2% | 0.1% |
| Citric Acid | — | — | — |
| Sodium Citrate | 0.015% | — | 0.015% |
| Glycerin | to 100% | to 100% | to 100% |
| pH Found | 4.80 | 5.00 | 4.80 |

Product: TRIAMTERENE AND HYDROCHLOROTHIAZIDE ORAL SOLUTION
Potency: Triamterene 25 mg/5 ml, Hydrochlorothiazide 25 mg/5 ml

| | Ex. #8 | Ex. #9 | Ex. #10 | Ex. #11 |
|---|---|---|---|---|
| Propylene Glycol (A) | 10% | 10% | 50% | 50% |
| Polyethylene Glycol-600 | 40% | 40% | — | — |
| Triamterene | 0.5% | 0.5% | 0.5% | 0.5% |
| Lactic Acid (85%) | 1% | 0.5% | 1% | 0.5% |
| Hydrochlorothiazide | 0.5% | 0.5% | 0.5% | 0.5% |
| Methylparaben | 0.1% | 0.1% | 0.1% | 0.1% |
| Propylene Glycol (B) | 1% | 1% | 1% | 1% |
| Polyethylene Glycol-400 | — | — | — | — |
| Polyethylene Glycol-600 | 4% | 4% | 4% | 4% |
| Sodium Benzoate | 0.1% | 0.1% | 0.1% | 0.1% |
| Purified Water (A) | 0.5% | 0.5% | 0.5% | 0.5% |
| Glycerin | 30% | 30% | 30% | 30% |
| Sodium Saccharin | 0.5% | 0.5% | 0.5% | 0.5% |
| Purified Water (B) | — | — | — | — |
| Chocolate Extract | 0.12% | 0.12% | 0.12% | 0.12% |
| Raspberry Oil | 0.02% | 0.02% | 0.02% | 0.02% |
| Anise Oil | 0.01% | 0.01% | 0.01% | 0.01% |
| Propylene Glycol (C) | 2% | 2% | 2% | 2% |
| FD&C Yellow #6 | — | — | — | — |
| FD&C Red #40 | 0.006% | 0.006% | 0.006% | 0.006% |
| Purified Water (C) | 0.6% | 0.6% | 0.6% | 0.6% |
| Citric Acid | 0.4% | 0.6% | 0.4% | 0.6% |
| Sodium Citrate | — | — | — | — |
| Glycerin | to 100% | to 100% | to 100% | to 100% |
| pH Found | 5.00 | 5.00 | 5.00 | 5.00 |

While there has been disclosed what is considered to be the preferred embodiment of the present invention, it is understood that various changes in the details may be made without departing from the spirit, or sacrificing any of the advantages of the present invention.

I claim:

1. A pharmaceutical solution of triamterene, for oral administration which is a liquid at room temperature comprising triamterene present in a pharmaceutically effective amount to provide a diuretic effect for those in need thereof, a glycol, lactic acid or an acid salt thereof, said glycol and lactic acid or acid salt thereof being present in an amount sufficient to maintain the triamterene in solution, and a pharmaceutically acceptable diluent.

2. The pharmaceutical solution of claim 1, wherein the triamterene is present in the range of from about 0.5 mg/ml to about 100 mg/ml.

3. The pharmaceutical solution of claim 1, wherein the triamterene is present in the range of from 5 mg/ml to about 10 mg/ml.

4. The pharmaceutical solution of claim 1, wherein the glycol is propylene glycol, polyethelene glycol or mixtures thereof and is present in the range of from about 1% by volume to about 50% by volume.

5. The pharmaceutical solution of claim 4, wherein the polyethylene glycol has a molecular weight in the range of from about 200 to about 6000.

6. The pharmaceutical solution of claim 1, wherein the diluent includes glycerin.

7. The pharmaceutical solution of claim 6, wherein glycerin is present in an amount up to about 55% by volume.

8. The pharmaceutical solution of claim 6, wherein the diluent is present in the range of from about 20% by volume to about 55% by volume.

9. The pharmaceutical solution of claim 1, wherein the lactic acid is present in the range of from about 0.1% to about 20%.

10. The pharmaceutical solution of claim 1, wherein the lactic acid is present in the range of from about 0.5% to about 5%.

11. A pharmaceutical solution of triamterene for oral administration which is a liquid at room temperature, comprising triamterene present in the range of from about 5 mg/ml to about 10 mg/ml, lactic acid or an acid salt thereof present in the amount of not less than about 1% for each 5 mg/ml of triamterene, an effective amount of glycol having a molecular weight of from about 200 to about 6000, said solution having a pH of from about 4 to about 6, and a pharmaceutically acceptable diluent.

12. The pharmaceutical solution of claim 11, wherein the triamterene is present in the range of from 5 mg/ml to about 10 mg/ml.

13. The pharmaceutical solution of claim 11, wherein the glycol is propylene glycol, polyethelene glycol or mixtures thereof and is present in the range of from about 1% by volume to about 50% by volume.

14. The pharmaceutical solution of claim 11, wherein the diluent is present in the range of from about 20% by volume to about 55% by volume.

15. The pharmaceutical solution of claim 14, wherein the diluent is glycerin.

16. The pharmaceutical solution of claim 15, and further comprising a pharmaceutically acceptable sweetening agent and a pharmaceutically acceptable preservative of methylparaben or sodium benzoate.

17. A diuretic and anti-hypertensive pharmaceutical solution for oral administration which is a liquid at room temperature, comprising triamterene present in a pharmaceutically effective amount to provide a diuretic effect for those in need thereof, hydrochlorothiazide present in a pharmaceutically effective amount to provide an anti-hypertensive effect for those in need thereof, a glycol, lactic acid or an acid salt thereof, said glycol and lactic acid or salt thereof being present in an amount sufficient to maintain the triamterene in solution, and a pharmaceutically acceptable diluent.

18. The diuretic and anti-hypertensive pharmaceutical solution of claim 17, wherein the triamterene is present in the range of from about 0.5 mg/ml to about 100 mg/ml.

19. The diuretic and anti-hypertensive pharmaceutical solution of claim 17, wherein hydrochlorothiazide is present in the range of from about 0.25 mg/ml to about 50 mg/ml.

20. The diuretic and anti-hypertensive pharmaceutical solution of claim 17, wherein triamterene is present in the range of from about 0.5 mg/ml to about 100 mg/ml and hydrochlorothiazide is present in the range of from about 0.25 mg/ml to about 50 mg/ml.

21. The diuretic and anti-hypertensive pharmaceutical solution of claim 20, wherein the glycol is propylene glycol, polyethelene glycol or mixtures thereof and is present in the range of from about 1% by volume to about 50% by volume.

22. The diuretic and anti-hypertensive pharmaceutical of claim 21, wherein the diluent includes glycerin and is present in the range of from about 20% by volume to about 55% by volume.

* * * * *